United States Patent
Marshall

(10) Patent No.: US 12,402,894 B2
(45) Date of Patent: Sep. 2, 2025

(54) UNIVERSAL KEYLESS GUIDED SURGERY SYSTEM

(71) Applicant: VERSAH, LLC, Jackson, MI (US)

(72) Inventor: Todd Marshall, Jackson, MI (US)

(73) Assignee: Versah, LLC, Jackson, MI (US)

( * ) Notice: Subject to any disclaimer, the term of this patent is extended or adjusted under 35 U.S.C. 154(b) by 649 days.

(21) Appl. No.: 17/634,201

(22) PCT Filed: Aug. 10, 2020

(86) PCT No.: PCT/US2020/045708
§ 371 (c)(1),
(2) Date: Feb. 9, 2022

(87) PCT Pub. No.: WO2021/030317
PCT Pub. Date: Feb. 18, 2021

(65) Prior Publication Data
US 2022/0313278 A1    Oct. 6, 2022

Related U.S. Application Data

(60) Provisional application No. 62/886,427, filed on Aug. 14, 2019.

(51) Int. Cl.
*A61B 17/16* (2006.01)
*A61B 17/17* (2006.01)
(Continued)

(52) U.S. Cl.
CPC .......... *A61B 17/1615* (2013.01); *A61C 1/084* (2013.01); *A61C 3/02* (2013.01);
(Continued)

(58) Field of Classification Search
CPC .......... A61C 5/44; A61C 1/082; A61C 1/084; A61C 1/08; A61C 8/0089; A61B 17/1615;
(Continued)

(56) References Cited

U.S. PATENT DOCUMENTS

| 569,896 A | 10/1896 | Van Cauwenberg |
| 1,095,185 A | 5/1914 | Broadbent et al. |

(Continued)

FOREIGN PATENT DOCUMENTS

| CH | 706593 A1 | 12/2013 |
| CN | 101652109 A | 2/2010 |

(Continued)

OTHER PUBLICATIONS

Translation of WO2007/065978 (Year: 2007).*

*Primary Examiner* — Thomas C Barrett
*Assistant Examiner* — Shannel Nicole Belk
(74) *Attorney, Agent, or Firm* — Endurance Law Group PLC

(57) ABSTRACT

A depth stop for a drilling tool to form a hole of predetermined depth. The depth stop includes an interface portion that couples directly to the shank of the osteotome via interlocking spur and groove features. The interface has a cap flange and a tapered skirt. The underside of the cap flange establishes a reference surface for a tubular key that slides onto the tapered skirt and is held there by friction. The skirt is formed with a relief directly under the cap flange to facilitate haptic confirmation of proper connection. Elongated irrigation windows in the key expose a domed transition on the osteotome, thereby facilitating irrigation. The depth stop can be used, optionally, with an alignment jig designed with a precision guide bushing. The guide bushing is semi-cylindrical and terminates with an internal abutment step against which the lower end of the key engages at full depth.

24 Claims, 10 Drawing Sheets

(51) Int. Cl.
  *A61B 90/00* (2016.01)
  *A61C 1/08* (2006.01)
  *A61C 3/02* (2006.01)
  *A61C 5/44* (2017.01)
(52) U.S. Cl.
  CPC .............. *A61C 5/44* (2017.02); *A61B 17/17* (2013.01); *A61B 2090/034* (2016.02)
(58) Field of Classification Search
  CPC ... A61B 17/17; A61B 17/176; A61B 17/1633; A61B 17/1673; Y10T 408/8925
  See application file for complete search history.

(56) References Cited

U.S. PATENT DOCUMENTS

| | | | |
|---|---|---|---|
| 1,105,154 | A | 7/1914 | Mcmillen |
| 3,562,913 | A | 2/1971 | Saffro |
| 4,710,075 | A | 12/1987 | Davison |
| 5,429,504 | A | 7/1995 | Peltier et al. |
| 5,482,410 | A | 1/1996 | Chambers |
| 5,882,151 | A * | 3/1999 | Wirth, Jr. .............. B23B 49/005 408/202 |
| 5,890,897 | A | 4/1999 | Kruger et al. |
| 5,941,706 | A | 8/1999 | Ura |
| 6,110,178 | A | 8/2000 | Zech et al. |
| 6,514,258 | B1 | 2/2003 | Brown et al. |
| 6,739,872 | B1 | 5/2004 | Turri |
| 6,869,282 | B2 | 3/2005 | Carmichael et al. |
| 6,951,562 | B2 | 10/2005 | Zwirnmann |
| 7,048,477 | B2 | 5/2006 | Abrams |
| 7,569,058 | B2 | 8/2009 | Zwirnmann |
| 7,771,143 | B2 | 8/2010 | Bharadwaj et al. |
| 8,197,481 | B2 | 6/2012 | Zwirnmann |
| 8,876,444 | B1 * | 11/2014 | Chanturidze ......... B23B 51/104 408/202 |
| 9,408,615 | B2 | 8/2016 | Fitz et al. |
| 9,421,108 | B2 | 8/2016 | Hunt |
| 10,016,255 | B2 * | 7/2018 | Lantz ..................... A61C 1/082 |
| 10,085,819 | B2 | 10/2018 | Lantz et al. |
| 2003/0233098 | A1 | 12/2003 | Markworth |
| 2004/0092940 | A1 | 5/2004 | Zwirnmann |
| 2006/0008332 | A1 * | 1/2006 | Greenberg ............ B23B 49/005 408/202 |
| 2006/0093988 | A1 | 5/2006 | Swaelens et al. |
| 2006/0100637 | A1 | 5/2006 | Rathbun et al. |
| 2007/0099150 | A1 * | 5/2007 | Muller ..................... A61C 3/02 433/165 |
| 2007/0298375 | A1 | 12/2007 | Hirsch et al. |
| 2008/0045965 | A1 | 2/2008 | Miller et al. |
| 2008/0287953 | A1 * | 11/2008 | Sers ....................... A61C 1/084 606/80 |
| 2009/0181340 | A1 | 7/2009 | Wolf et al. |
| 2009/0326536 | A1 | 12/2009 | Pynsent |
| 2010/0062389 | A1 | 3/2010 | Drews et al. |
| 2010/0067996 | A1 | 3/2010 | Hsu |
| 2010/0173259 | A1 | 7/2010 | Vogel et al. |
| 2010/0297574 | A1 | 11/2010 | Llop et al. |
| 2010/0311006 | A1 | 12/2010 | Lancieux et al. |
| 2011/0054483 | A1 * | 3/2011 | Howlett ............. A61B 17/1617 606/96 |
| 2011/0208195 | A1 | 8/2011 | Palti et al. |
| 2011/0238071 | A1 * | 9/2011 | Fernandez-Scoma ....................... A61C 1/084 606/80 |
| 2012/0109140 | A1 * | 5/2012 | Akutsu .................. A61C 1/084 606/86 R |
| 2013/0071811 | A1 | 3/2013 | Groscurth et al. |
| 2013/0084540 | A1 | 4/2013 | Yoshihara et al. |
| 2014/0093838 | A1 | 4/2014 | Carmichael et al. |
| 2015/0265373 | A1 | 9/2015 | Jamison |
| 2018/0161124 | A1 | 6/2018 | Huwais |
| 2019/0029695 | A1 | 1/2019 | Huwais |

FOREIGN PATENT DOCUMENTS

| | | | |
|---|---|---|---|
| CN | 104039252 A | 9/2014 | |
| DE | 3800482 A1 | 7/1989 | |
| EP | 1867297 A1 | 12/2007 | |
| EP | 2712302 B1 | 12/2014 | |
| EP | 2954878 B1 | 8/2016 | |
| JP | S63216560 A | 9/1988 | |
| JP | H07106205 B2 | 11/1995 | |
| JP | 2001212158 A | 8/2001 | |
| JP | 2009165799 A | 7/2009 | |
| JP | 2014136307 A | 7/2014 | |
| KR | 20060037925 A | 5/2006 | |
| KR | 20060096849 A | 9/2006 | |
| KR | 20110016602 A | 2/2011 | |
| KR | 101501236 B1 | 3/2015 | |
| WO | WO-2007065978 A1 * | 6/2007 | ............ A61B 17/17 |
| WO | WO-2016187493 A1 * | 11/2016 | ............ A61B 17/16 |
| WO | WO-2018071863 A1 * | 4/2018 | ............ A61B 17/58 |

* cited by examiner

UNIVERSAL KEYLESS GUIDED SURGERY SYSTEM

CROSS REFERENCE TO RELATED APPLICATIONS

This application claims priority to Provisional Patent Application 62/886,427 filed on Aug. 14, 2019.

BACKGROUND OF THE INVENTION

Field of the Invention

The invention relates generally to tools for forming a hole in a host material to receive an implant or anchor or other fixation device, and more specifically toward a novel depth stop that limits penetration of the drilling tool to a predetermined depth and also helps orient the drilling tool.

Description of Related Art

An implant is a medical device manufactured to replace a missing biological structure, to support a damaged biological structure, or to enhance an existing biological structure. Bone implants may be found throughout the human skeletal system, including dental implants in a jaw bone to replace a lost or damaged tooth, vertebral implants used to secure cages, joint implants to replace damaged joints such as hips and knees, and reinforcement implants installed to repair fractures and remediate other deficiencies, to name but a few. The placement of an implant often requires a preparation into the bone using either hand osteotomes or precision drills with highly regulated speed to prevent burning or pressure necrosis of the bone. After a variable amount of time to allow the bone to grow on to the surface of the implant (or in some cases to grow onto a fixture portion of an implant), sufficient healing will enable a patient to start rehabilitation therapy or return to normal use or perhaps the placement of a restoration or other attachment feature.

In the example of a dental implant, preparation of a hole or osteotomy is required to receive a bone implant. The depth of an osteotomy is determined by the amount of axial movement that the clinician imparts on a drilling tool as he or she inserts the drilling tool into the bone tissue. If the depth of the bore is too long, it can puncture the sinus cavity in the maxillary, or the mandibular canal (which contains nerves and blood vessels) in the mandible. Likewise, the roots of adjacent teeth also can be adversely affected by an improperly formed osteotomy. Conversely, if the depth of the bore is too short, the implant may not properly seat and/or too much stress will be placed on the host material attempting to seat the implant.

To ensure that a drilling tool is inserted into the bone to a known depth, the drilling tool may contain markings that signify specific depths. For example, a drilling tool may have bands of etched markings that indicate the bore depth at several locations. The use of these visual markers is, of course, limited to the clinician's ability to see the mark as the drilling tool is being inserted into the patient's mouth. Accordingly, the clinician is required to keep his or her visual attention on the depth marker as he or she slowly proceeds with the axial movement that causes the drilling tool to be inserted deeper and deeper into the bone. Visibility in such cases can be obscured by irrigation fluid and tools and other obstructions, making the traditional visual markers sometimes difficult to use.

The prior art discloses various types of stop elements that prohibit insertion of a drill into the bone tissue beyond a predetermined depth. The methods employed by these prior are schemes are either difficult/cumbersome to use, or are expensive to produce. A few notable examples are described below.

U.S. Publication No. 2007/0099150 to Daniele discloses a depth stop key for a dental drill. The shank of the drill has a series of grooves. Pawls at the top of the stop key selectively engage the grooves in the shank to set the drilling depth. Drilling depth is adjusted by moving the stop key up or down along the drill shank.

German patent document DE3800482 to List teaches a depth stop for a surgical drill. A series of annular ribs are formed along the drill shank. A stop key fitted with a spring and ball locking mechanism sequentially snaps into the annular ribs to set the drilling depth.

U.S. Pat. No. 7,569,058 to Ralph discloses an adjustable depth stop for a surgical device used to form pre-threaded holes in bone. A series of annular ribs are formed along the length of the tap shank. A stop key fitted with flexible pawls sequentially snaps into the annular ribs to set the tap depth. A screw-on locking cap threads over the flexible pawls to secure them in an adjusted position.

U.S. Pat. No. 6,739,872 to Turri discloses an adjustable depth stop for a surgical drill in which a screw thread is formed on or attached to the drill shank. A sleeve-like stop key mates with the screw thread to allow the axial position of the key to be adjusted by turning.

Common disadvantages perceived among the prior art are many, and include lack of ability to be installed on and removed from any drilling tool. Rather, in each case a specially manufactured drilling tool is required. Another common disadvantage is that multiple grooves and/or screw threads must be formed in the tool shank. For high-speed applications, the multiple grooves risk weakening the shank with multiple stress-concentrating nodes that invite unwanted vibrations in use. The multiple grooves/threads also add to manufacturing expense. And furthermore, each groove/thread in the shank represents a hard-to-clean location for post-operative sterilization prior to re-use. Multiple grooves in the tool shank compound this concern, resulting in increased time and effort required during the customary sterilization and cleaning processes. Still further disadvantages of the prior art depth-stop concepts relate to the overall lack of suitability for retrofit use across a wide range of drilling tools marketed by different manufacturers. And yet further, none of the prior art depth-stop concepts are well-suited for use with the growing demand for guided surgery applications.

Korean patent document KR20060096849 to Hsieh discloses a guided surgery system in which a mouth jig has a guide feature to provide location and orientation control. Hsieh teaches the diameter of the guide feature can be reduced by adhering an additional magnetic guide bushing. However, the Hsieh system is not coordinated for use with a depth-stop feature, thereby making it difficult or cumbersome to utilize depth control in combination with guided surgery.

There is therefore a need in the art for an improved depth stop that prohibits insertion of a surgical drilling tool or bur into the bone tissue beyond a predetermined depth, and which can be used conveniently in combination with a jig for guided surgery.

BRIEF SUMMARY OF THE INVENTION

According to a first aspect of the invention, a depth stop is provided for use with a drilling tool for forming a hole of predetermined depth in a host material. The depth stop comprises an interface connectable to the shank of a surgical drilling tool. The interface has a partially tubular shape defining an interior region. The interface extends axially between top and bottom ends thereof. The interface includes a cap flange adjacent the top end. A tapered skirt extends axially from the cap flange toward the bottom end. The skirt has a relief directly below the cap flange. A tubular key has an inner diameter and an outer diameter. The key extends between an upper end and a lower end. A stop ring is formed at the lower end. The inner diameter of the key is sized for interference fit surrounding the widest diameter of the tapered lower portion of the skirt and clearance fit surrounding the relief of the skirt.

According to a second aspect of the invention. A combined osteotome and depth stop for forming a hole of predetermined depth in a host material, comprises: a shank establishing a longitudinal axis of rotation. The shank has an elongated cylindrical shape defining a shank diameter and extends between an upper distal end and a lower transition end. An annular groove disposed at a predetermined intermediate axial location along the shank between the distal and transition ends. A domed transition formed at the transition end of the shank. The domed transition has a diameter greater than the shank diameter. A body extends from the domed transition. The body has an apical end remote from the shank. A plurality of flutes disposed about the body. An interface connectable to the shank. The interface has a partially tubular shape defining an interior region. The interface extends axially between top and bottom ends thereof. A lateral pocket extends continuously through interface from the top end to the bottom end and intersecting the interior region. A spur disposed on the interior region and configured to engage with the groove in the shank. The interface includes a cap flange adjacent the top end. A tapered skirt extends axially from the cap flange toward the bottom end. The skirt has a relief disposed directly adjacent the cap flange. A tubular key has an upper end and a lower end. A stop ring is formed at the lower end. The key has an inner diameter and an outer diameter. The inner diameter of the key being sized for interference fit at the widest diameter of the tapered skirt and clearance fit surrounding the relief of the skirt.

The invention accommodates an improved depth stop that effectively limits insertion of a drilling tool into the host material beyond a predetermined depth, and which can optionally be used in combination with a jig for guided surgery.

BRIEF DESCRIPTION OF THE SEVERAL VIEWS OF THE DRAWINGS

These and other features and advantages of the present invention will become more readily appreciated when considered in connection with the following detailed description and appended drawings, wherein.

DETAILED DESCRIPTION OF THE INVENTION

Figure 1:
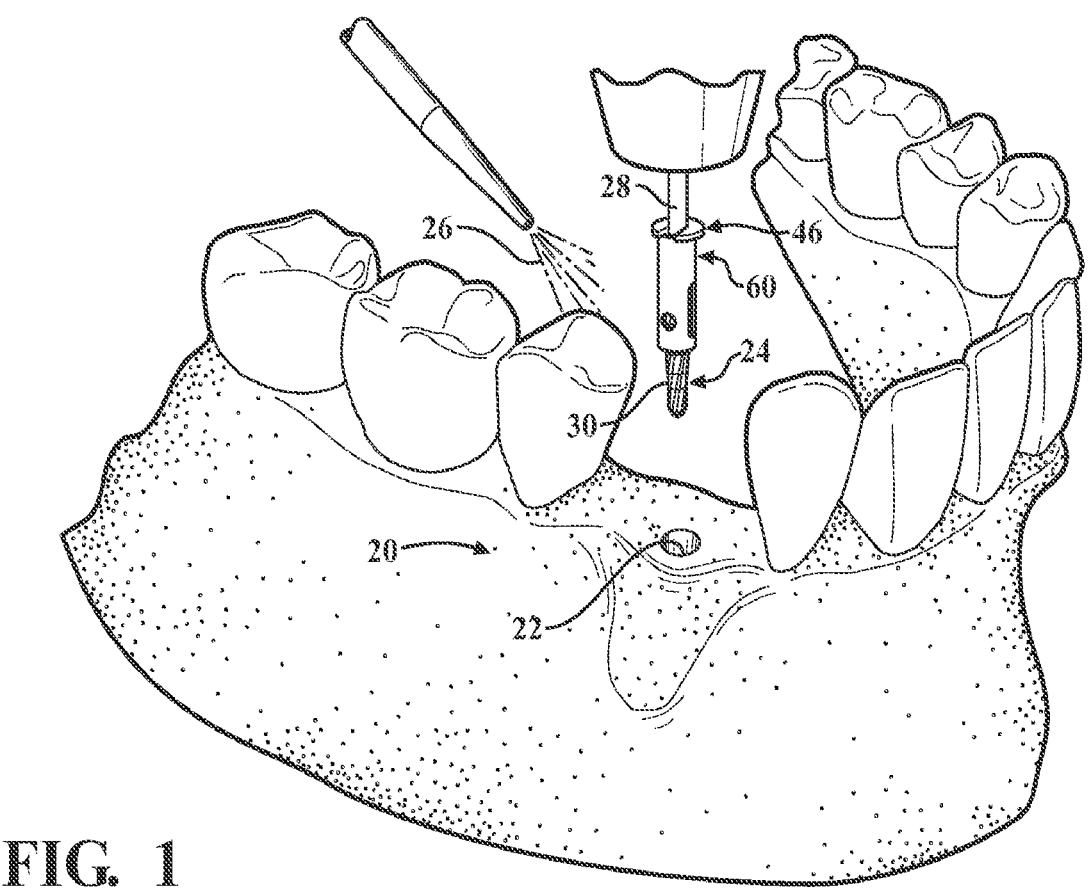
FIG. 1 shows an exemplary application of the present invention at an edentulous jaw site in the process of being prepared with a drilling tool fitted with a depth stop according to the present invention.

Referring to the figures, wherein like numerals indicate like or corresponding parts throughout the several views, FIG. 1 shows the exemplary periodontal context of an edentulous jaw site 20, in which an osteotomy 22 must be prepared in order to receive an implant (not shown). In addition to dental applications, the principles of this invention are applicable to general surgical and orthopedic applications, as well as non-medical uses in manufacturing and other industries requiring formation of holes to precise depths. Thus, although the term osteotomy infers a hole in bone, the term is intended to be interpreted in a wider sense to encompass any hole formed in any type of host material.

One method of preparing an osteotomy 22 is described in U.S. Pat. No. 9,028,253 issued May 12, 2015 to Huwais. According to the method of U.S. Pat. No. 9,028,253, a pilot hole is first bored into the recipient bone at the edentulous jaw site 20. The small bored pilot hole is then expanded using a series of progressively larger osteotomes 24 rotated at high-speed by a hand-held surgical drill motor (not shown). To reiterate, although the term osteotome infers a tool used to form a hole in bone, the term is intended to be interpreted in a wider sense to encompass any tool used to form a hole in any type of host material. The rotary osteotomes 24 are designed to auto-graft the host material, e.g., bone, directly into the sidewalls of the osteotomy 22 while forcibly expanding the osteotomy 22 using modulated pressure combined with copious irrigation 26, resulting in a smooth, highly densified osteotomy 22 capable of providing high initial stability for a subsequently placed implant or other fixture device. However, it will be appreciated that the inventive features of this invention are not exclusively limited to use with the rotary osteotome 24 like that depicted in the drawings. Instead, the principles of this invention could be used, instead, with traditional drilling tools. Nevertheless, the present invention is well-adapted for use with the high-speed rotary condensing osteotome 24 and is therefore referenced as a preferred example herein.

The rotary osteotome 24 is described in U.S. Pat. No. 9,326,778 issued May 3, 2016, and also in WO 2015/138842 published Sep. 17, 2015, both to Huwais. Generally stated, the auto-grafting osteotome 24 includes a shank 28 and a working end or body 30. The shank 28 is an elongated cylindrical shaft that establishes a longitudinal axis of rotation A for the rotary osteotome 24 when driven at high speed (e.g., greater than 200 rpm: typically in the range of 800-1500 rpm) by the drill motor. The cylindrical shape of the shank 28 defines a shank diameter S (FIG. 4) and extends between an upper distal end and a lower transition end. A drill motor engaging interface 32 is formed at the upper distal end of the shank 28 for connection to the drill motor. Of course, the particular configuration of the interface 32 may vary depending on the type of drill motor used, and in some cases may even be merely a smooth or hex portion of the shank 28 against which the jaws of a collet grip.

Figure 2A:
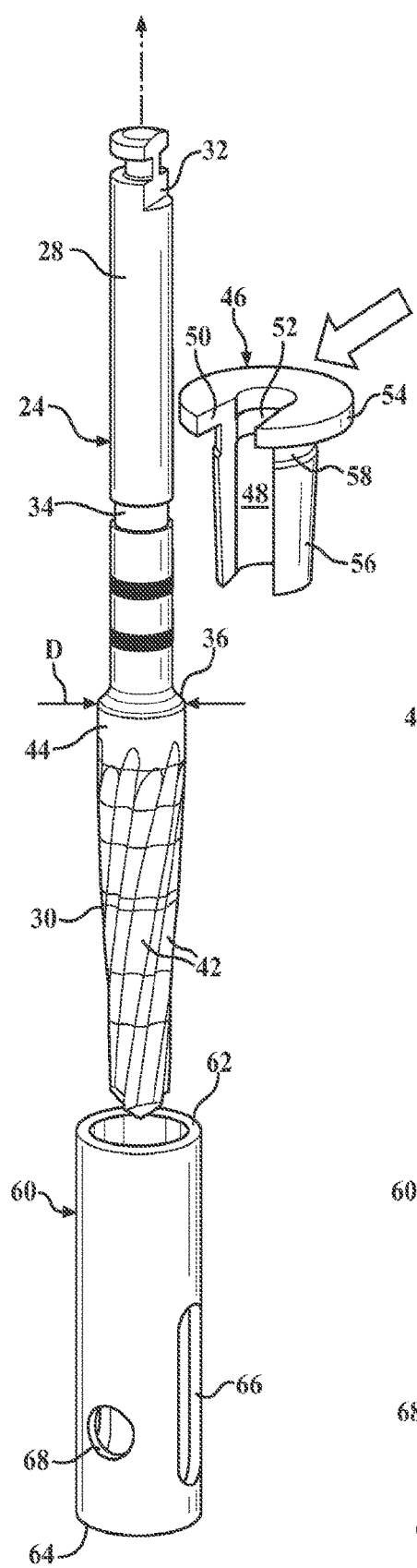
FIG. 2A is an exploded view of an osteotome and depth stop according to one embodiments of the present invention.

An annular groove 34 is disposed at a predetermined intermediate axial location along the shank 28 between the upper distal and lower transition ends, as best seen in FIG. 2A. The groove 34 is preferably shallow, with relatively square inset corners. The longitudinal length (i.e., width) of the groove 34 may be in the range of about 10% to 100% of the shank diameter S, although widths of greater or lesser dimensions are possible.

Figure 15A:
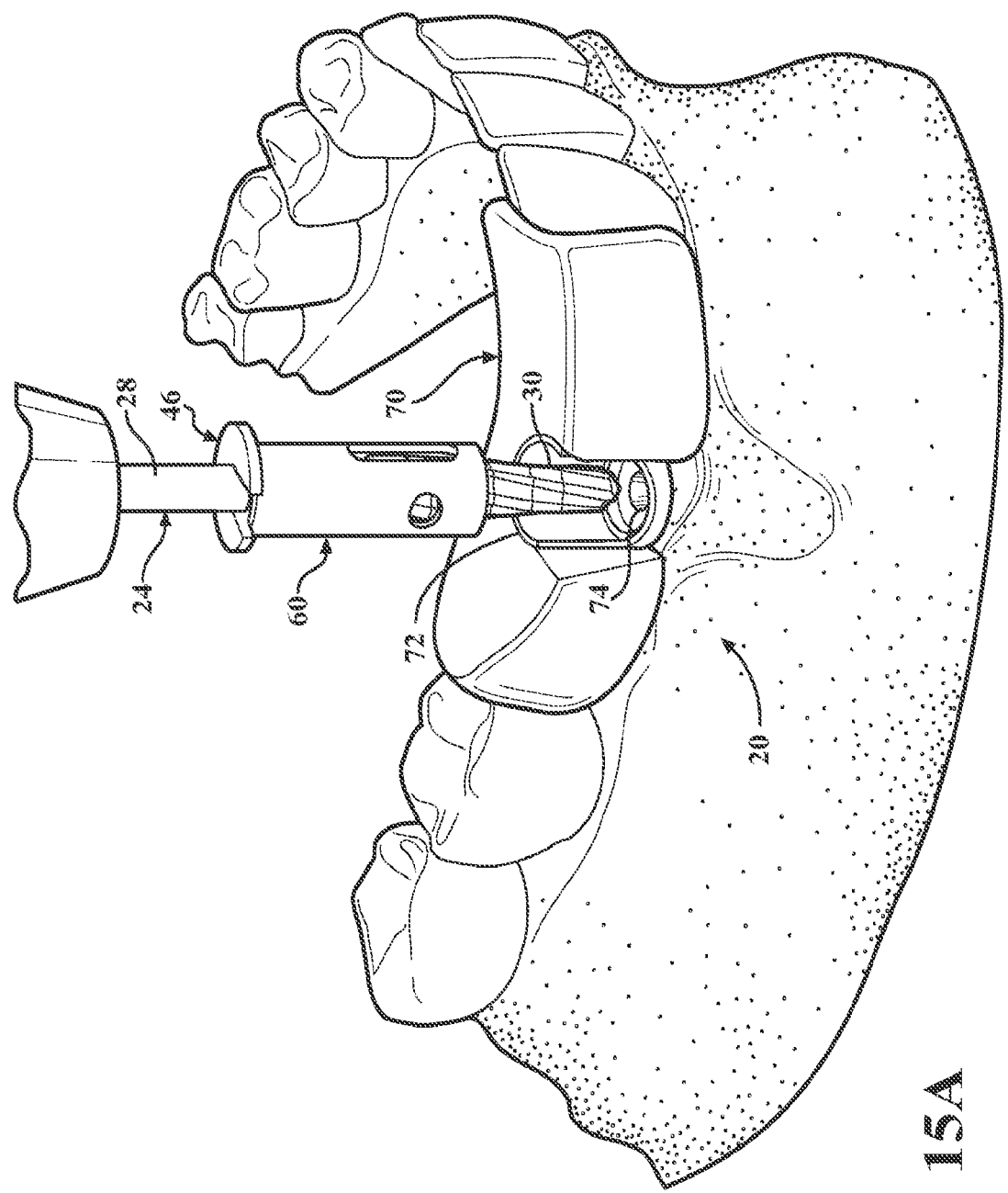
FIG. 15A is a view as in FIG. 1 showing an osteotomy in the process of being prepared with an auto-grafting rotary osteotome fitted with a key according to the present invention, and wherein a guided surgery jig is used to provide alignment assistance.
Figure 15B:
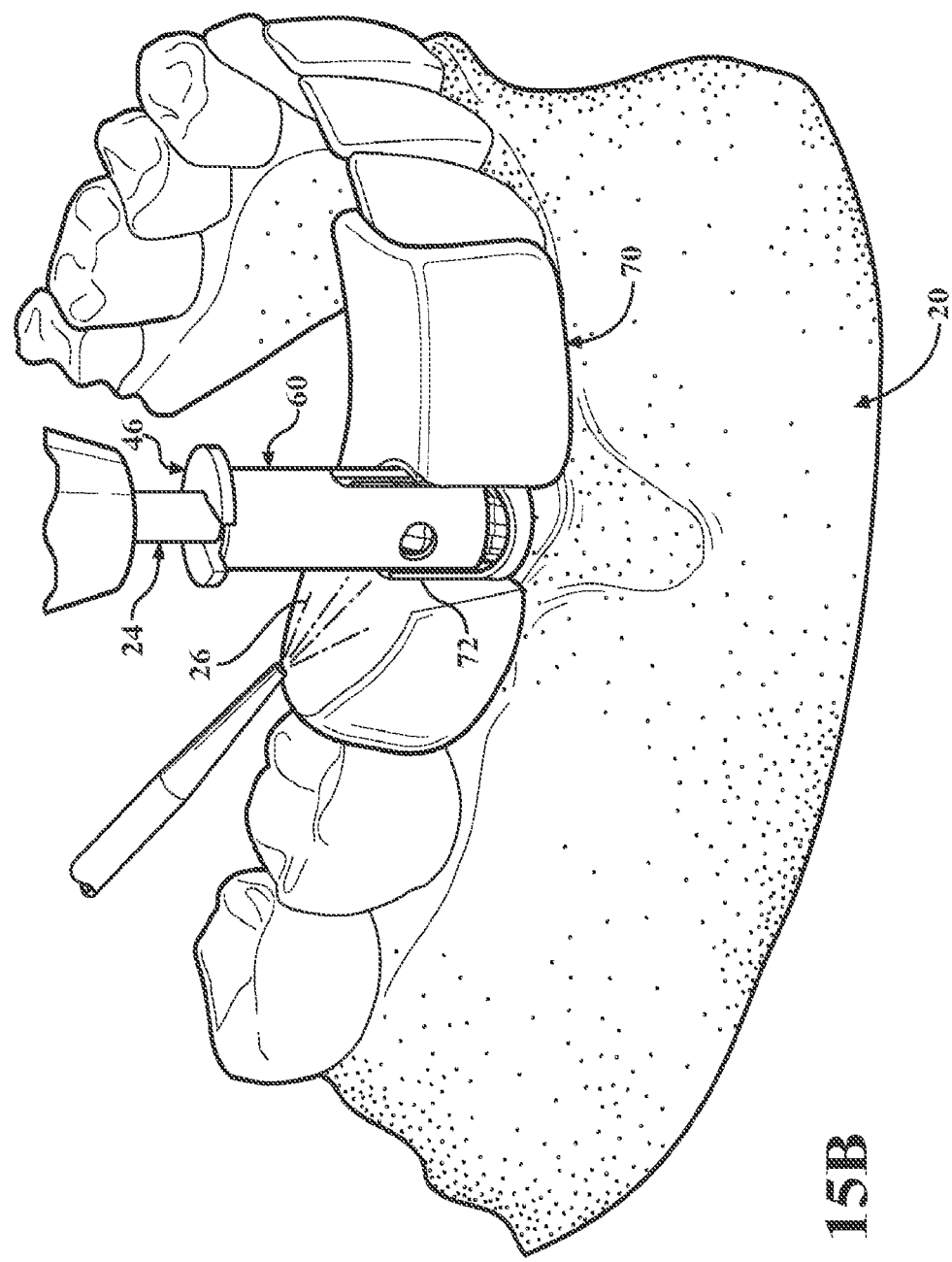
FIG. 15B is a view as in FIG. 15A showing the rotary osteotome at full depth as limited by the key 60 and the concurrent application of irrigating fluid.

A domed transition 36 is formed at the lower transition end of the shank 28. The domed transition 36 has a diameter D (FIG. 2A) that is greater than the shank diameter S. The domed transition 36 may be formed with a filleted, tapered, hemispherical, ogee or other hydro-dynamic shape to help spread and evenly distribute the irrigating fluid as the surgeon irrigates with water (or saline, etc.) during use. Irrigation of the osteotomy site 22, as depicted at 26 in FIGS. 1 and 15B, is especially important when using an auto-grafting type rotary osteotome 24 so as to enable certain beneficial hydrodynamic effects and manage heat.

The body 30 of the osteotome 24 joins to the shank 28 at the domed transition 36. The body 30 can be viewed as extending from the domed transition 36 toward a leading tip referred to as the apical end 38. The apical end 38 is thus remote from the shank 28, with the aforementioned groove 34 being located along the shank 28 at a predetermined distance from the apical end 38 for reasons that will be described. The body 30 of the osteotome 24 has either a straight profile or a conically tapered profile decreasing from a maximum diameter adjacent the shank 28 to a minimum diameter adjacent the apical end 38. The working length or effective length of the body 30 is proportionally related to its taper angle and, in cases where the osteotomy 22 is formed by a sequence of progressively larger osteotomes 24, is also related to the size and number of osteotomes 24 in a surgical kit. Preferably, in cases where the body 30 is tapered, all osteotomes 24 in a sequence will have the same taper angle, and the diameter at the upper end of the body 30 for one osteotome 24 will be approximately equal to the diameter adjacent the apical end 38 of the body 30 for the next larger size osteotome 24.

Figure 2B:
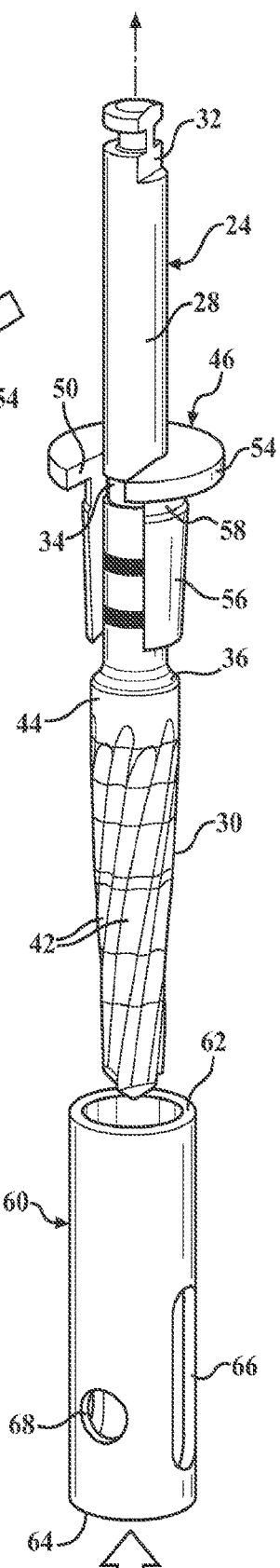
FIG. 2B is a view as in FIG. 2A showing a progression of the assembly process in which the interface portion of the depth stop is connected to the shank of the osteotome.
Figure 4:
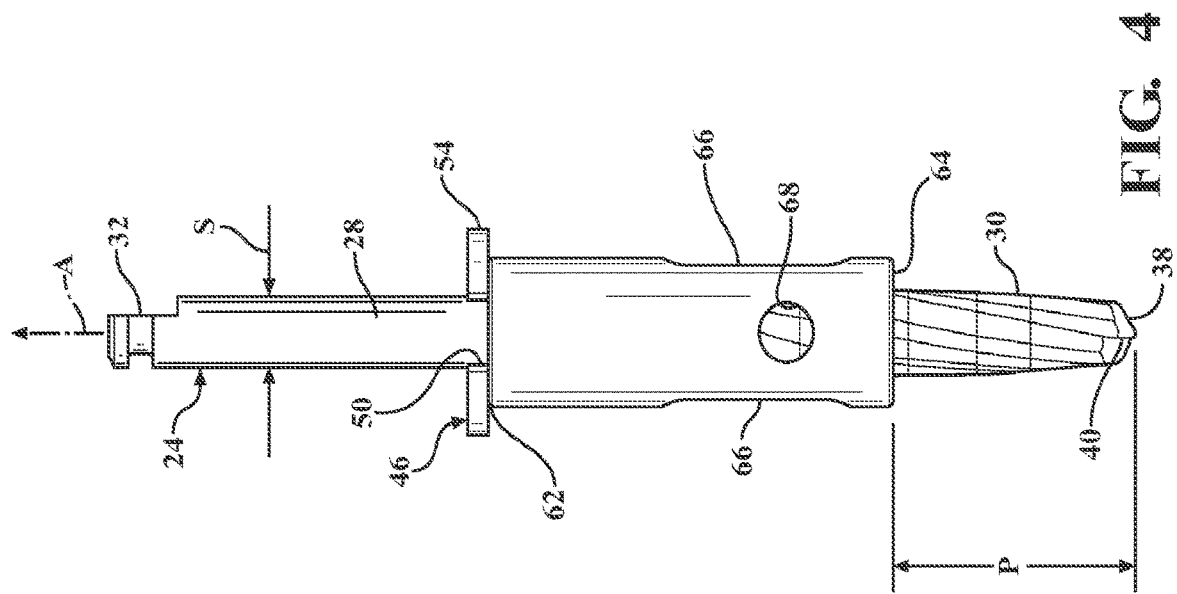
FIG. 4 is a side elevation of the depth stop assembled to an osteotome and revealing an exposed length of the osteotome body with which to form a hole.
Figure 14:
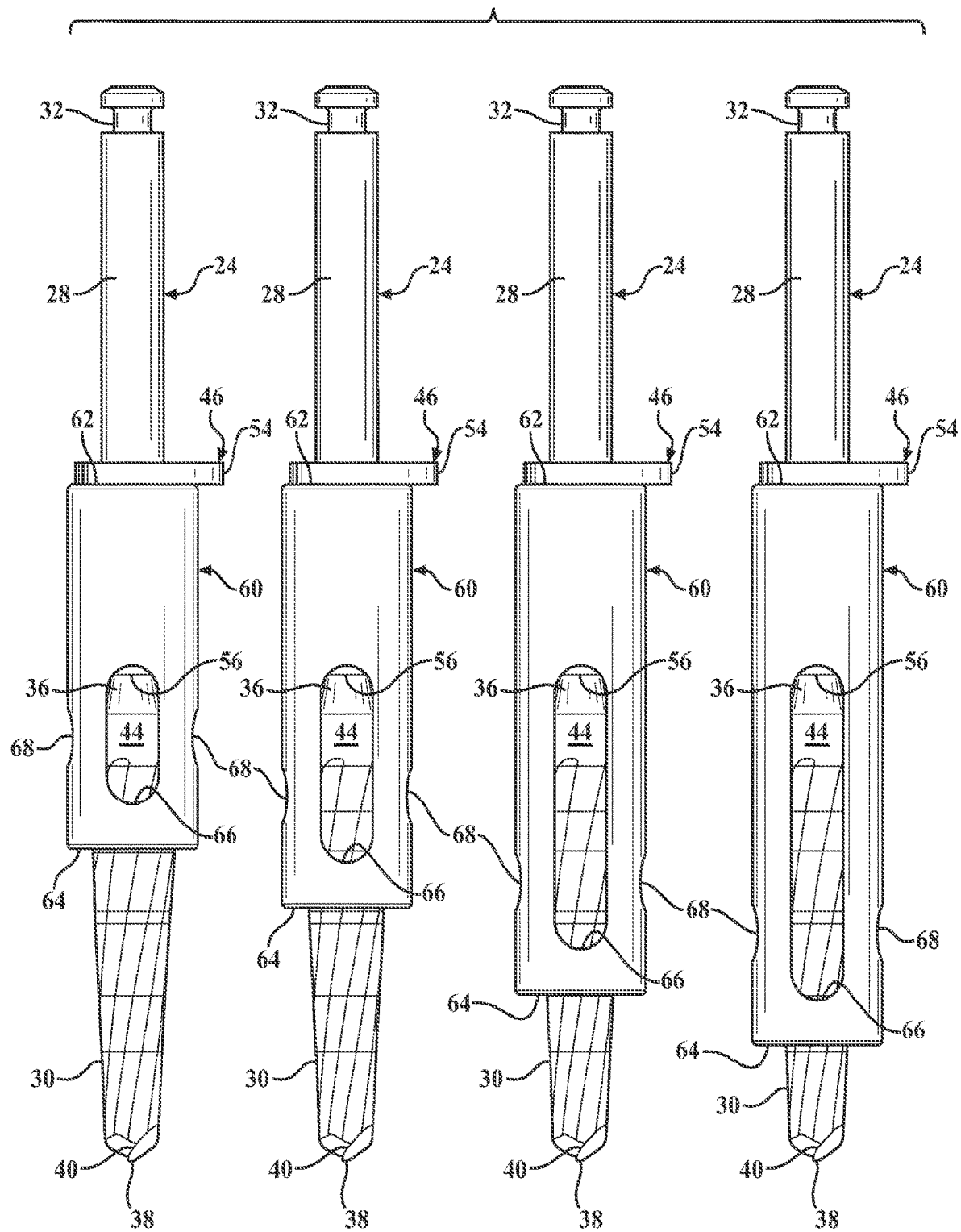
FIG. 14 shows four osteotomes of identical length each fitted with a depth stop of different length.

The apical end 38 may include one or more grinding lips 40 (FIGS. 4 and 14). A plurality of grooves or flutes 42 are disposed about the body 30. The flutes 42 are preferably, but not necessarily, equally circumferentially arranged about the body 30. Each the flute 42 has a cutting face on one side thereof that defines a rake angle and a densifying face on the other side thereof defines a heel-side angle, as described in detailed in US2019/0029695 to Huwais, published Jan. 31, 2019. The flutes 42 have an axial length and radial depth. A stopper section 44 of the body 30 is disposed between the flutes 42 and the domed transition 36, as best seen in FIGS. 2A and 2B. A rib or land is formed between adjacent flutes 42, in alternating fashion. Thus, a four-flute 42 osteotome 24 will have four interposed lands, a ten-flute 42 osteotome 24 will have ten interleaved lands, and so forth. Each land forms a working edge. In some embodiments, the working edge helically twists about the body 30. Depending on the rotational direction of the osteotome 24, the working edge either functions to cut or condense the host material. That is, when the osteotome 24 is rotated in the cutting direction, the working edges slice and excavate the host material. However, when the osteotome 24 is rotated in the condensing (non-cutting) direction and pushed into the osteotomy 22 with modulating pressure, the working edges compress and radially displace the host material with little-to-no cutting. This compression and radial displacement are exhibited as gentle pushing of the osseous structure laterally outwardly in a condensation mechanism.

The invention is directed toward an accessory depth stop for an osteotome 24, and optionally combined with a jig or guide system, for forming a hole 22 of predetermined depth in the host material.

Figure 8:
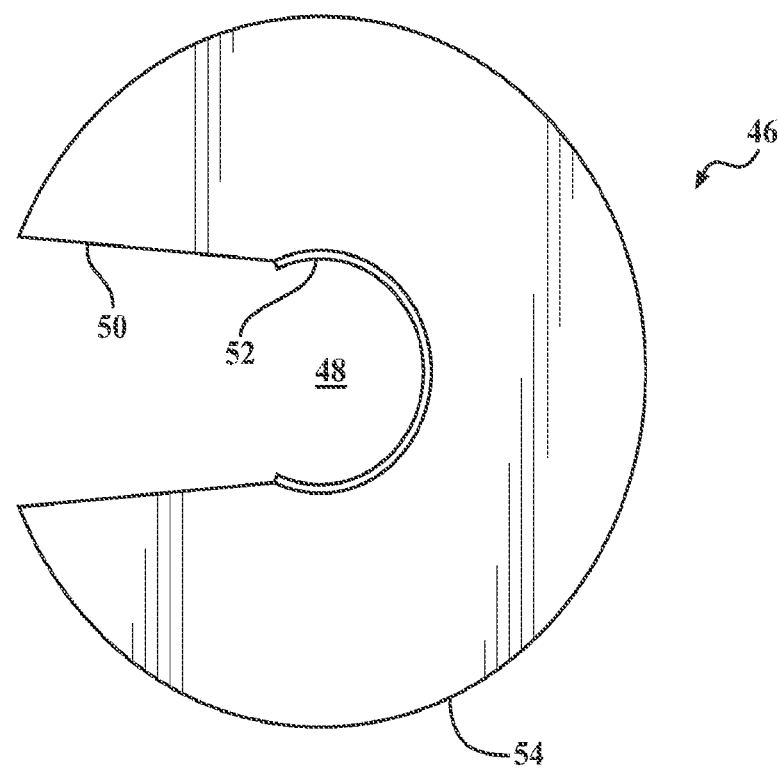
FIG. 8 is a top view of the interface of FIG. 5.
Figure 9:
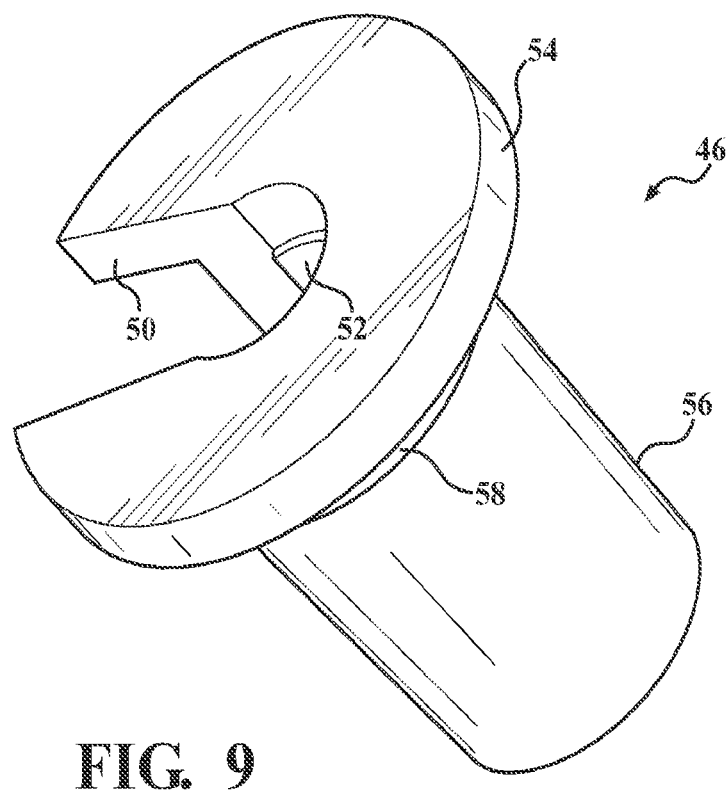
FIG. 9 is a perspective view of the interface of FIG. 5.

The accessory depth stop includes an interface, generally indicated at 46. The interface 46 has a partially tubular shape within which is defined an interior region 48. The interface 46 extends axially between top and bottom ends. When the interface 46 is connected to the shank 28, the bottom end of the interface 46 is spaced apart from the domed transition 36, as shown in FIG. 2B, so as to avoid disturbing its hydrodynamic properties. That is to say, the interface 46 does not overlap the domed transition 36 when joined to the osteotome 24. A lateral pocket 50 extends like a full-length slot continuously through the interface 46 from the top end to the bottom end, intersecting with and exposing the interior region 48. A spur 52 disposed on the interior region 48 is configured to engage with the groove 34 in the shank 28. In the example of FIG. 8, the spur 52 has a C-shape configured to seat in-between the inset corners of the groove 34. The interface 46 includes a cap flange 54 adjacent the top end. A skirt 56 extends axially from the cap flange 54 toward the bottom end. The interior region 48 extends fully through both the cap flange 54 and skirt 56 to form a full-length passage for the shank 28.

The interface 46 is connectable to the shank 28 at its groove 34 through either axial or lateral coupling motion. The spur 52 self-locks on the osteotome shank 28 by seating itself inside the groove 34. Thus, whether the interface 46 is loaded onto the osteotome 24 through axial or lateral motion, the spur 52 will engage in the groove 34 to establish a secure connection. It can be understood, therefore, that the spur 52 serves as a precise axial locating feature for the interface 46 on the shank 28. And more specifically, the spur 52 accurately locates the underside of the cap flange 54 relative to the apical end 38 of the osteotome 24.

Figure 2C:
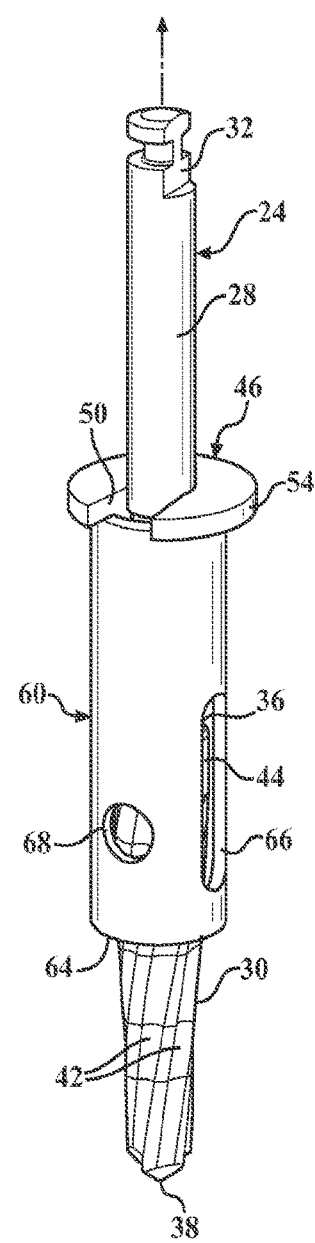
FIG. 2C is a view as in FIG. 2B showing a further progression of the assembly process in which the key is fully fitted to the interface.

Returning to FIGS. 2A-C, lateral connection of the interface 46 to the osteotome shank 28 is enabled by the pocket 50, which is a full-length gap along the side of the interface 46. The pocket 50 is perhaps best shown in FIGS. 6-9 having a tapered receiving area at it passes through the radially outer portion of the cap flange 54. At its widest point along the outer edge of the cap flange 54, the pocket 50 is wider than the shank diameter S. This enables the osteotome shank 28 to easily slide into the pocket 50 during the lateral coupling maneuver. The pocket 50 progressively narrows in the radially inward direction. The narrowest portion of the pocket 50 occurs at the point of intersection with the interior region 48. At this narrowest point, the pocket 50 is slightly smaller than the shank diameter S and slightly smaller than the diameter of the interior region 48 to facilitate a snap-fit connection.

The exterior surface of the skirt 56 is preferably tapered and includes a relief 58 disposed directly under the cap flange 54. The relief 58 may be axially aligned with the spur 52 as can be appreciated from FIGS. 6 and 7. In the preferred embodiment, the top edge of the spur 52 is generally axially aligned with lower edge (i.e., under surface) of the cap flange 54 as made apparent in the cross-sectional view of FIG. 6.

Figure 3:
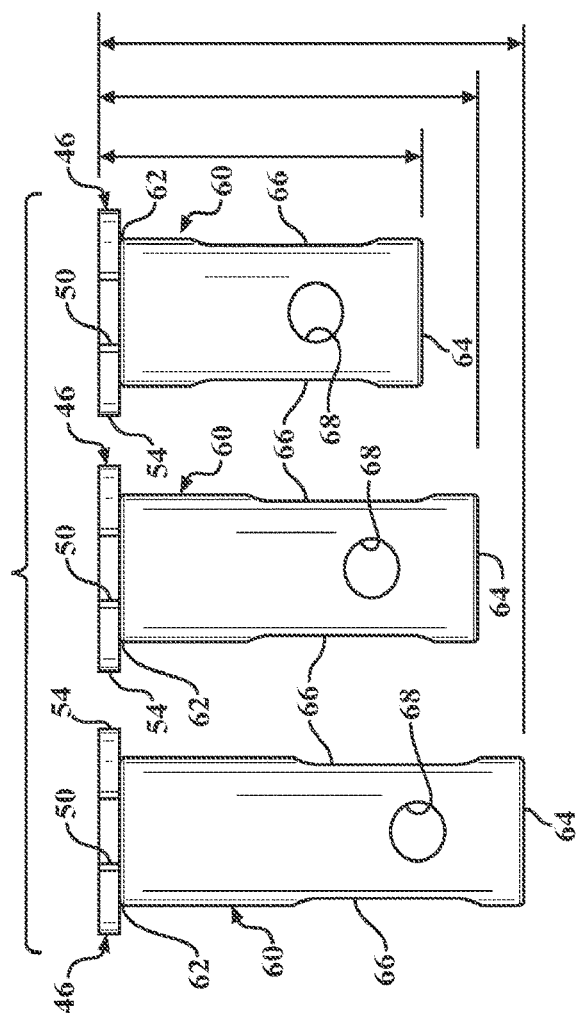
FIG. 3 shows three keys of different lengths for selective use in a hole forming operation.
Figure 5:
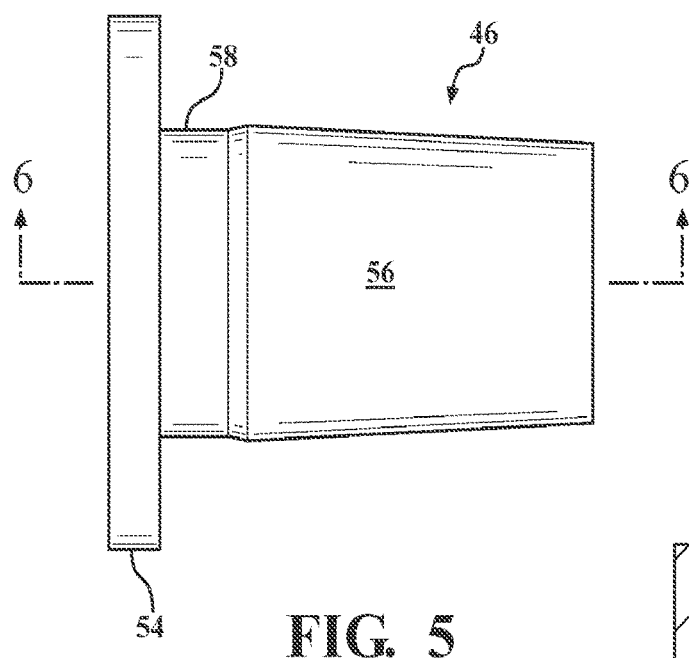
FIG. 5 is a side view of an interface according to one embodiment of the invention.
Figure 6:
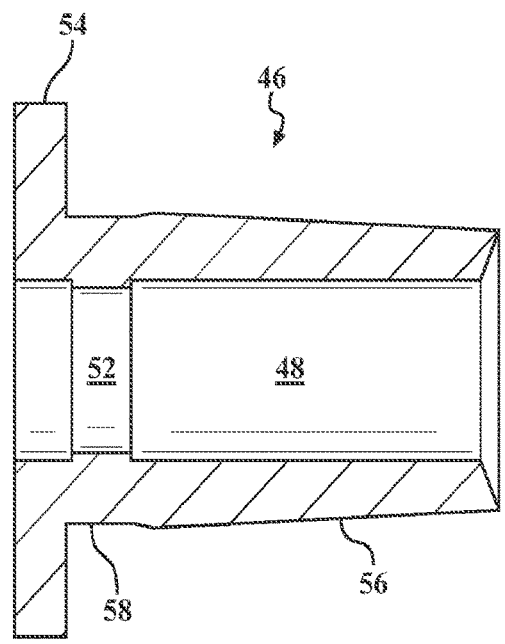
FIG. 6 is a cross-sectional view taken generally along lines 6-6 in FIG. 5.
Figure 7:
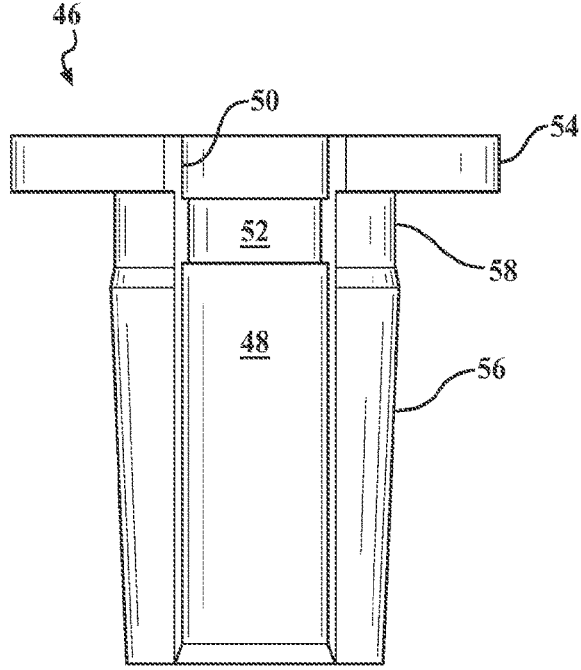
FIG. 7 is a front elevation view of the interface of FIG. 5.

The interface 46 is intended to be used with an array of different "fixed-length" keys 60 to achieve respective penetration depths P (FIG. 4) for the apical end 38 of the osteotome 24. In the example of FIG. 3, three keys 60 are shown, each having a different respect length. FIG. 14 shows four osteotomes 24 of identical length each fitted with a depth stop having keys 60 of different lengths. From this view, it is easily seen how the exposed length of body 30 is directly affected by the length of the key 60, whereby depth of penetration P of the apical end 38 is controlled. In certain periodontal applications, for example, it may be advantageous to provide a kit containing five different length keys 60 configured to achieve net penetration depths P of 6 mm, 8 mm, 10 mm, 11.5 mm and 13 mm, respectively. Of course, many variations are possible.

Figure 12:
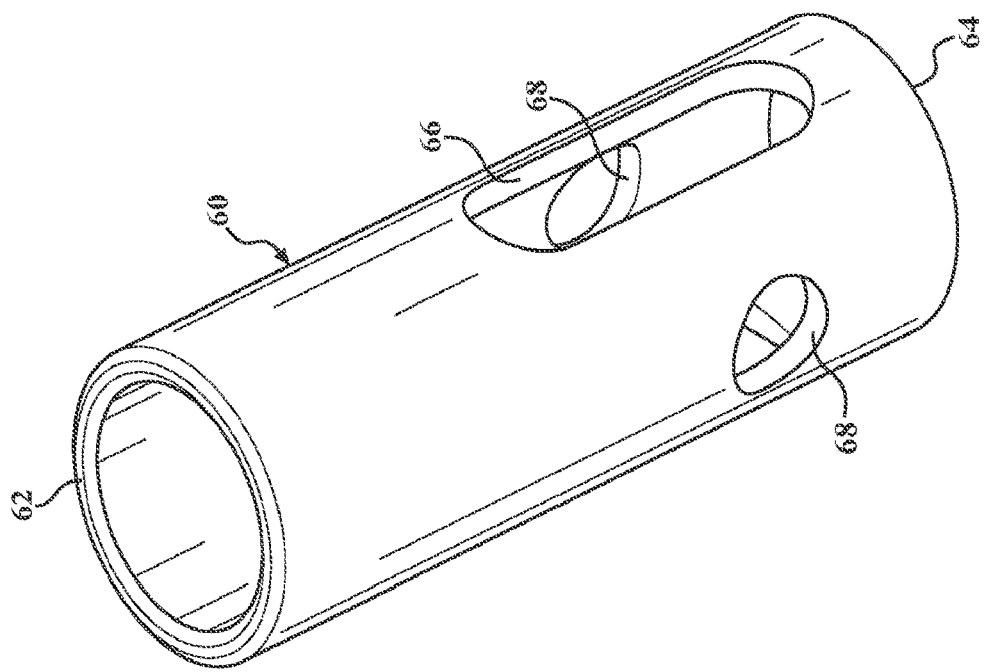
FIG. 12 is a perspective view of the key of FIG. 10.
Figure 11:
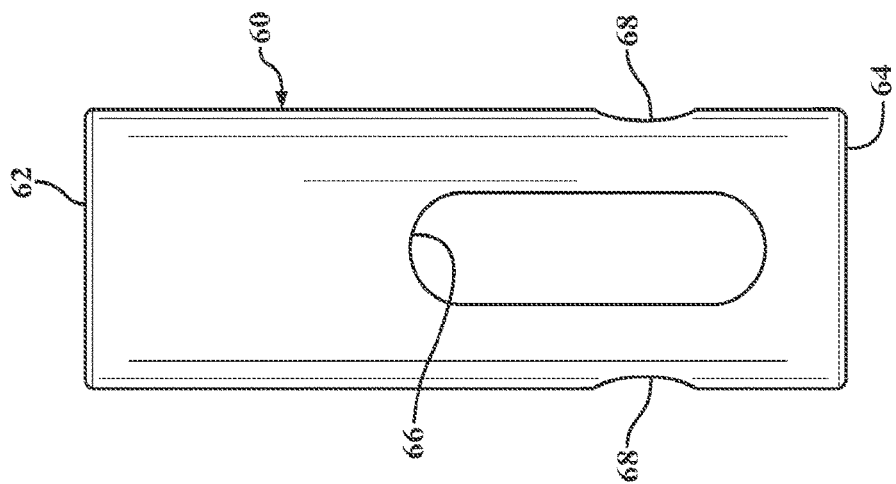
FIG. 11 is a side elevation view of the key of FIG. 10.
Figure 10:
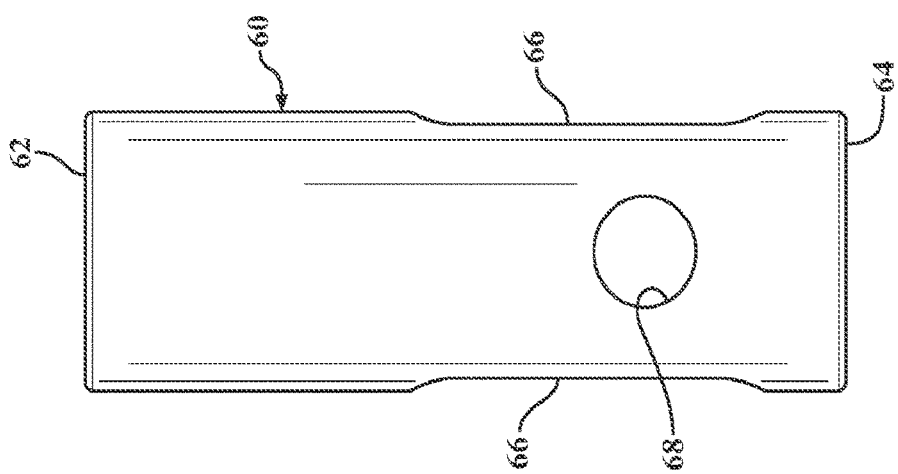
FIG. 10 is a front elevation view of a key according to one embodiment of the invention.

A key 60 is shown in detail in FIGS. 10-12 extending between upper 62 and lower 64 ends. A stop ring is formed at the lower end 64. Configured in a generally tubular shape, the key 60 has an inner diameter and an outer diameter. The inner diameter of the key 60 is sized for interference fit surrounding the widest diameter of the skirt 56. This then yields an advantageous clearance fit surrounding the relief 58. This relationship can be best seen in FIG. 13B. Thus, keys 60 are held in place on the interface 46 by friction established in a localized annular region of the skirt 56, namely at the widest portion of its taper. A user can quickly remove and install each key 60 by simple axial motion, as suggested by FIGS. 2B-C and 13A-B. The tapered shape of the skirt 56 facilitates connection and disconnection by establishing an annular rim of contact along the bottom edge of the relief 58. The interior surface of the key 60 will make full circular contact at or near this point of maximum diameter. A noticeable tactile (haptic) feedback will be sensed when installing and removing the key 60 as its upper edge traverses the annular rim of contact.

The relief 58 is configured in the form of a neck or undercut to provide clearance for the top of the key 60 to seat positively against the underside of the cap flange 54. The undersurface of the cap flange 54 provides a critical locating function. It is desirable that the user be able to tactilely discern, i.e., via haptic sensation, when the upper end 62 of the key 60 makes contact with the cap flange 54. The user must be able to feel, with confidence, the moment in time when the key 60 has reached full insertion over the interface 46. During the process of installing a key 60 over a tapered skirt 56, the user senses gradually increasing resistance due to friction. This is because the exterior of the skirt 56 is tapered and the fit becomes progressively tighter. Even if the increase in resistance is very minute, the human hand is able to sense it. However, once the upper end 62 of the key 60 enters the relief 58, the resistance will remain constant. The human hand will readily perceive the change from increasing resistance to constant resistance and intuitively inform the user that full insertion depth is near. As soon as the upper end 62 contact the underside of the cap flange 54, the resistance will abruptly jump thus informing the user that full insertion depth has been achieved. Were it not for the relief 58, a user installing a key 60 would be more likely to inadvertently stop short of reaching the cap flange 54, in which case the net depth of the osteotomy 22 would be shallower than intended.

By axially aligning the relief 58 with the spur 52, any flexing in the interface 46 caused by force transmissions through the shank 28 will be less inclined to affect the key 60 due to the clearance space in the immediate vicinity. When the key 60 installed, the interface 46 becomes trapped in place on the shank 28 and cannot be removed. The interface 46 can only be installed on/removed from the shank 28 without an attached key 60. The key 60 therefore provides a beneficial interlocking function so that they interface 46 cannot inadvertently become disconnected or axially shifted along the shank 28 in use, thereby better assuring that a precise hole depth P will be achieved.

The key 60 is preferably fitted with one or more irrigation windows to permit pass-through of irrigation fluid. The irrigation windows may be configured in many different shapes, including but not limited to alternating oval and circular holes. In the illustrated examples, oval holes form axially elongated irrigation windows 66, whereas circular holes form small irrigation windows 68. In the preferred embodiment, at two diametrically opposed elongated irrigation window 66 is disposed in the key 60, and also two diametrically opposed small irrigation windows 68. Of course, other arrangements are certainly possible.

Figure 13A:
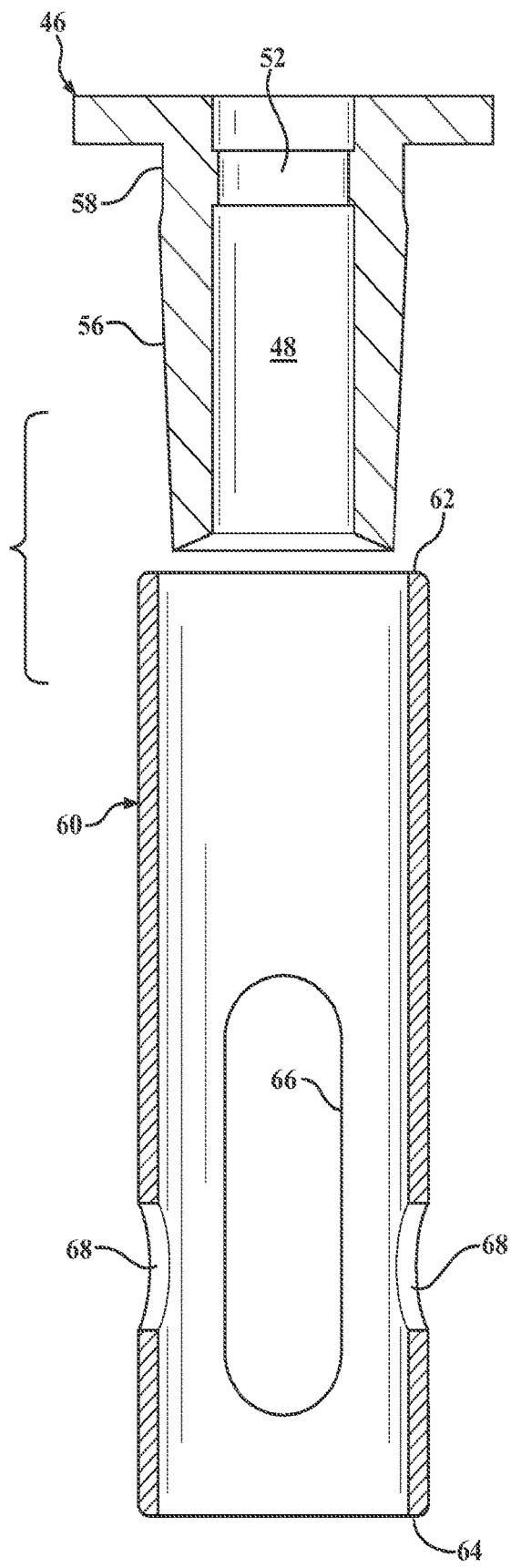
FIG. 13A is an exploded view of a depth stop, in cross-section.
Figure 13B:
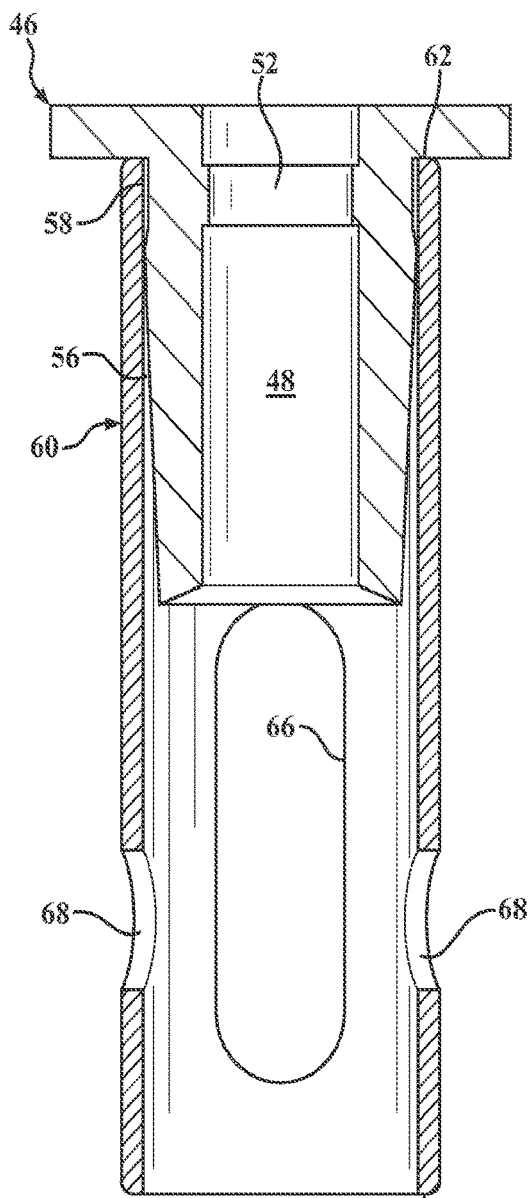
FIG. 13B is a view as in FIG. 13A showing the key and interface portions of the depth stop assembled to one another.

When a key 60 is connected to an interface 46, the elongated irrigation window 66 exposes the bottom end of the interface 46 therethrough, as can be seen in FIGS. 13B and 14. And when an assembled key 60 and interface 46 are coupled to an osteotome 24, the elongated irrigation windows 66 expose at least a portion of the domed transition 36 therethrough, as can be clearly seen in FIG. 14. The entirety of the stopper section 44 is also fully exposed through the elongated irrigation windows 66. By exposing the domed transition 36 in this fashion, irrigation fluid 26 can directly reach the domed transition 36 while in use. As a result, irrigating fluid 26 will achieve the desired hydrodynamic effects and properly manage heat build-up. Likewise, the important stopper section 44 can also receive proper irrigation 26.

While the illustrations may seem to suggest only one diameter key 60, it will be understood that in practice several diameters of keys 60 may be made available for applications in which implants/anchors of various sizes are placed. For example, the key 60 may be offered in sizes of small, medium, large and extra-large diameters. Drills or osteotomes 24 up to a certain small diameter may be accommodated by small diameter keys 60, up to a certain medium diameter may be accommodated by medium keys 60, up to a certain large diameter may be accommodated by the large diameter keys 60, and drills or osteotomes 24 of all diameters may be accommodated by the extra-large diameter key 60. A typical surgical procedure to form an osteotomy 22 will call for a certain final diameter drill or osteotome 24.

FIG. 1 shows use of the depth stop, i.e., interface 46 and key 60 assembly, in the exemplary application of "free hand" placing a dental implant. That is to say, the skill of the surgeon is relied upon to orient the angular approach of the osteotome 24 into the host material, which is bone in this example. When the stop ring or lower end 64 of the key 60 touches the surface of the host material, full penetration depth P has been reached. In these cases, the cylindrical shape of the key 60 provides a beneficial visual orientation aide for the surgeon. That is to say, the cylindrical key 60 will provide edge-line references that are parallel to the drilling axis A. It will be more intuitively apparent to the surgeon whether the drilling approach is properly oriented, as compared with use of the osteotome 24 without the depth stop. Optionally, the depth stop may be used in conjunction with an alignment jig 70 configured to be secured relative to the target drilling location in the host material. FIGS. 15A and 15B, display such a jig 70 in one highly exemplary form. Those of skill in this art will appreciate that a suitable jig 70 can take many different forms.

In the illustrated examples, the jig 70 includes a precision formed guide bushing 72. The guide bushing 72 can be seen having a semi-cylindrical alignment valley that is specially adapted to receive the key 60 with a smooth, slack-free sliding fit. The semi-cylindrical shape of the guide bushing 72 allows the body 30 of the osteotome 24 to be laterally placed into the guide bushing 72, which could be helpful in some tight operating quarters such as the mouth of a small person. Furthermore, the semi-cylindrical shape of the guide bushing 72 allows both visual monitoring of the key 60 as it descends and also access for irrigation fluid 26 to flood the irrigation windows 66, 68 even at full depth. At the base of the alignment valley can be seen an internal abutment step 74. The abutment step 74 may be configured in the shape of a full annular surface adapted to engage the stop ring of the key 60 when the apical tip 38 has reached a predetermined penetration limit in the host material. The full annular shape of the internal abutment step 74 provides stability.

The shape of the guide bushing 72 may include low-cut scallop directly above the abutment step 74 to eliminate or minimize stress-concentrating sharp internal corners. The scallop extends from the alignment valley so as to partially surround the thin protruding portion of the abutment step 74. This scallop also helps to strengthen the guide bushing 72 so that its shape is maintained even after autoclaving and other high-temperature procedures that might otherwise provoke some dimensional distortions. Nevertheless, a substantial majority of the alignment valley remains open and laterally accessible.

It will be understood that the internal diameter of the guide bushing 72 will be matched to the outer diameter of the key 60. Thus, a small size guide bushing 72 will be used in conjunction with a small size key 60; a large size guide bushing 72 will be used in conjunction with a large size key 60; and so forth. It must be understood that the dimensional attributes described herein are offered as examples only for applications within dental field of use. Of course, other dimensional attributes are possible, especially when the present invention is adapted for use in general orthopedic (i.e., non-dental) applications, or in altogether non-medical (e.g., industrial) applications.

The foregoing invention has been described in accordance with the relevant legal standards, thus the description is exemplary rather than limiting in nature. Variations and modifications to the disclosed embodiment may become apparent to those skilled in the art and fall within the scope of the invention.

What is claimed is:

1. A depth stop for use with a drilling tool for forming a hole of predetermined depth and orientation in a host material, said depth stop comprising:
    an interface connectable to the shank of a surgical drilling tool, said interface having a partially tubular shape defining an interior region, said interface extending axially between top and bottom ends thereof, said interface including a cap flange adjacent said top end, a tapered skirt extending axially from said cap flange toward said bottom end, wherein said interface includes a lateral pocket extending continuously therethrough from said top end to said bottom end and intersecting said interior region to enable connection of said interface to the shank with a lateral coupling motion,
    a tubular key having an inner diameter and an outer diameter, said key extending between an upper end and a lower end, a stop ring formed at said lower end, and
    said inner diameter of said key being sized for interference fit surrounding said skirt, and said upper end of said key configured to seat against said cap flange.

2. The depth stop of claim 1, further including a spur disposed on said interior region.

3. The depth stop of claim 2, wherein said spur has a generally C-shape.

4. The depth stop of claim 2, wherein said skirt has a relief disposed directly adjacent said cap flange, said relief being axially aligned with said spur.

5. The depth stop of claim 1, further including at least one axially elongated irrigation window is disposed in said key, said axially elongated irrigation window exposing said bottom end of said interface therethrough.

6. The depth stop of claim 5, further including at least one small irrigation window disposed in said key.

7. The depth stop of claim 1, wherein said skirt includes a relief disposed adjacent said cap flange, said inner diameter of said key being sized for a clearance fit surrounding said relief.

8. The depth stop of claim 7, wherein said relief is disposed directly adjacent said cap flange.

9. The depth stop of claim 7, wherein said skirt has a tapered lower portion in which a widest diameter thereof is adjacent said cap flange, said inner diameter of said key being sized for interference fit surrounding said widest diameter of said tapered lower portion of said skirt.

10. A combined osteotome and depth stop assembly for forming a hole of predetermined depth and orientation in a host material, comprising:
    a shank establishing a longitudinal axis of rotation, said shank having an elongated cylindrical shape defining a shank diameter and extending between an upper distal end and a lower transition end, an annular groove disposed at a predetermined intermediate axial location along said shank between said distal and transition ends, a domed transition formed at said transition end of said shank, said domed transition having a diameter greater than said shank diameter,
    a body extending from said domed transition, said body having an apical end remote from said shank, a plurality of flutes disposed about said body,
    an interface selectively connectable to said shank with a lateral coupling motion, said interface having a partially tubular shape defining an interior region, said interface extending axially between top and bottom ends thereof, a lateral pocket extending continuously through interface from said top end to said bottom end and intersecting said interior region to enable the lateral coupling motion connection of said interface to said shank, a spur disposed on said interior region and configured to engage with said groove in said shank, said interface including a cap flange adjacent said top end, a skirt extending axially from said cap flange toward said bottom end, said skirt having a relief disposed adjacent said cap flange, a tubular key having an upper end and a lower end, a stop ring formed at said lower end, said key having an inner diameter and an outer diameter, said inner diameter of said key being sized for interference fit around said skirt and clearance fit surrounding said relief, and said upper end of said key configured to seat against said cap flange.

11. The assembly of claim 10, wherein said bottom end of said interface is spaced apart from said domed transition with said interface connected to said shank.

12. The assembly of claim 10, further including at least one axially elongated irrigation window disposed in said key, said axially elongated irrigation window exposing said domed transition therethrough with said interface connected to said shank.

13. The assembly of claim 12, wherein said axially elongated irrigation window exposes said bottom end of said interface therethrough.

14. The assembly of claim 12, further including at least one small irrigation window disposed in said key.

15. The assembly of claim 10, wherein said relief is axially aligned with said spur.

16. The assembly of claim 10, wherein said spur has a C-shape.

17. The assembly of claim 10, wherein said annular groove in said shank is formed with inset corners, and said spur is seated in-between said inset corners of said groove.

18. The assembly of claim 10, further including a jig configured to be secured relative to a target drilling location in the host material, said jig including a guide bushing, said guide bushing having a semi-cylindrical alignment valley adapted to receive said key.

19. The assembly of claim 18, wherein said alignment valley includes an internal abutment step.

20. The assembly of claim 19, wherein, said internal abutment step has a full annular surface adapted to engage said stop ring of said key.

21. The assembly of claim 10, wherein said relief is disposed directly adjacent said cap flange.

22. The assembly of claim 10, wherein said skirt has a tapered lower portion in which a widest diameter thereof is adjacent said cap flange, said inner diameter of said key being sized for interference fit surrounding said widest diameter of said tapered lower portion of said skirt.

23. A combined osteotome and depth stop assembly for forming a hole of predetermined depth and orientation in a host material, comprising:

a shank establishing a longitudinal axis of rotation, said shank having an elongated cylindrical shape defining a shank diameter and extending between a upper distal end and a transition end, a drill motor engaging interface disposed at said upper distal end of said shank, an annular groove disposed at a predetermined intermediate axial location along said shank between said upper distal and transition ends, said groove having inset corners, said groove having a longitudinal length in the range of about 10% to 100% of said shank diameter, a domed transition formed at said transition end of said shank, said domed transition having a diameter greater than said shank diameter, a body extending from said domed transition, said body having an apical end remote from said shank, a plurality of flutes disposed about said body, an interface selectively connectable to said shank with a lateral coupling motion, said interface having a partially tubular shape defining an interior region, said interface extending axially between top and bottom ends thereof, a lateral pocket extending continuously through interface from said top end to said bottom end and intersecting said interior region to enable the lateral coupling motion connection of said interface to said shank, a spur disposed on said interior region and configured to engage with said groove in said shank, said spur having a C-shape, said spur seated in-between said inset corners of said groove, said interface including a cap flange adjacent said top end, a skirt extending axially from said cap flange toward said bottom end, said skirt having a skirt exterior, said skirt having a relief disposed directly adjacent said cap flange, said relief being axially aligned with said spur, said skirt tapering from a widest diameter adjacent said relief, said bottom end of said interface spaced apart from said domed transition with said interface connected to said shank, and a tubular key having an upper end and a lower end, a stop ring formed at said lower end, said key having an inner diameter and an outer diameter, said inner diameter being sized for interference fit surrounding said widest diameter of said tapered skirt and clearance fit surrounding said relief of said skirt, said upper end of said key configured to seat against said cap flange, at least one axially elongated irrigation window disposed in said key, said axially elongated irrigation window exposing said domed transition therethrough.

24. The assembly of claim 23, further including a jig configured to be secured relative to a target drilling location in the host material, said jig including a guide bushing, said guide bushing having a semi-cylindrical alignment valley adapted to receive said key, said alignment valley including an internal abutment step, said internal abutment step having a full annular surface adapted to engage said stop ring of said key.

* * * * *